(12) United States Patent
Fischmann

(10) Patent No.: US 12,306,167 B2
(45) Date of Patent: May 20, 2025

(54) METHOD FOR CREATING GEOMETRIC FRESHWATER SANITARY ZONES WITHIN LARGE WATER BODIES

(71) Applicant: Crystal Lagoons Technologies, Inc., Miami, FL (US)

(72) Inventor: Fernando Fischmann, Miami, FL (US)

(73) Assignee: CRYSTAL LAGOONS TECHNOLOGIES, INC., Miami, FL (US)

(*) Notice: Subject to any disclaimer, the term of this patent is extended or adjusted under 35 U.S.C. 154(b) by 0 days.

(21) Appl. No.: 18/411,002

(22) Filed: Jan. 11, 2024

(65) Prior Publication Data

US 2024/0264137 A1    Aug. 8, 2024

Related U.S. Application Data

(60) Provisional application No. 63/482,875, filed on Feb. 2, 2023.

(51) Int. Cl.
*G01N 33/18* (2006.01)
*C02F 1/00* (2023.01)
*C02F 103/00* (2006.01)

(52) U.S. Cl.
CPC .............. *G01N 33/18* (2013.01); *C02F 1/008* (2013.01); *C02F 2103/007* (2013.01)

(58) Field of Classification Search
CPC .... G01N 33/18; C02F 1/008; C02F 2103/007
USPC ............... 73/432.1; 702/1, 5, 33; 137/1, 802
See application file for complete search history.

(56) References Cited

U.S. PATENT DOCUMENTS

| | | |
|---|---|---|
| 9,776,888 B1 | 10/2017 | Kurani et al. |
| 10,725,438 B1 * | 7/2020 | Marsousi ............... G06V 10/25 |
| 2011/0210076 A1 | 9/2011 | Fischmann Torres |
| 2012/0091069 A1 | 4/2012 | Fischmann T. |
| 2014/0111332 A1 | 4/2014 | Przybylko et al. |
| 2015/0125212 A1 | 5/2015 | Fischmann |
| 2017/0191237 A1 | 7/2017 | Fishmann Torres |

(Continued)

FOREIGN PATENT DOCUMENTS

BR    102018068943 A2 *  1/2019 ................ C02F 1/14

OTHER PUBLICATIONS

International Search Report for Application No. PCT/US24/11211 mailed Apr. 17, 2024.

*Primary Examiner* — Robert R Raevis
(74) *Attorney, Agent, or Firm* — MERCHANT & GOULD P.C.

(57) ABSTRACT

Geometric freshwater sanitary areas are created within large water bodies without the use of physical barriers to separate the area. A coordinated reference system (CRS) is used for mapping the defined geometric freshwater area in terms of its position; the definition of directional vectors (DVs) for the introduction of freshwater into the geometric freshwater area through inlet elements to achieve a minimum renewal rate of such geometric freshwater area; the application of a Comparative Water Renewal Index (CWRI); and the application of a Homogeneity Index (HI) based on the mixing conditions of the geometric freshwater area and its required homogenous conditions. Utilizing the processes together generate geometric freshwater sanitary areas that are suitable for bathing (direct contact purposes).

16 Claims, 3 Drawing Sheets

(56) References Cited

U.S. PATENT DOCUMENTS

2020/0047076 A1 2/2020 Fischmann
2020/0217098 A1 7/2020 Shalon et al.

\* cited by examiner

METHOD FOR CREATING GEOMETRIC FRESHWATER SANITARY ZONES WITHIN LARGE WATER BODIES

CROSS-REFERENCE TO RELATED APPLICATIONS

This application is non-provisional and claims the benefit of U.S. Provisional Patent Application No. 63/482,875, filed Feb. 2, 2023. The disclosure of the priority application in its entirety is hereby incorporated by reference into the presence application.

FIELD OF THE INVENTION

The present invention relates to the field of recreational water bodies, mainly comprising man-made water bodies larger than 4,000 m$^2$ in water surface and having more than 5,000 m$^3$ in water volume, where such water bodies include design features, structural elements, and operational standards to allow direct contact purposes, such as swimming and bathing, at least in some non-physically confined portion of the large water body.

BACKGROUND OF THE INVENTION

The practice of water-based recreational activities, such as swimming and the practice of aquatic water sports, has continued to grow and gain popularity in recent years. This has driven the artificial recreational water feature sector's growth, with increasing consumer inclinations towards water activities. For example, an independent study found that the participation in outdoor swimming throughout the UK increased by 1.5-3 times between 2019 and 2020. Overall, worldwide trends have seen an upsurge in outdoor swimming mainly related to health and recreational benefits.

The use of large water features for direct contact recreational purposes does not come without risk, as natural water bodies have their own natural treatment systems and processes (such as biological equilibrium) to achieve a water quality that may be suitable for swimming. However, sometimes the natural processes cannot keep up with contamination events or eutrophication processes that deteriorate water quality and hence impair the ability of such water features to provide a suitable water quality for direct contact purposes. Even further, there are ecological impacts on freshwater ecosystems that may result from water-based recreational activities.

Given these challenges related to the use of natural water features, the market for man-made large water features has grown greatly over the past recent years, in order to provide large water features that allow direct contact recreational activities such as swimming. However, conventional swimming pool technology is neither prepared nor suitable to provide solutions for larger-than-average water features, mainly because of how conventional swimming pools are built and operated around the world.

Conventional swimming pool technology around the world is known to usually require intensive filtration of its complete water volume, normally at a rate of 4 times per day, which means that the complete swimming pool water volume must be filtered every 6 hours to achieve removal of particles and contaminants that are suspended in the swimming pool water. Further, not only the filtration of the complete water volume is needed, but an efficient filtration must be achieved, taking care that the actual volume of the pool is filtered in a homogeneous manner, so that all bits and portions of the swimming pool water are indeed withdrawn from the pool, sent to a filtration system, and returned to the swimming pool. This means that conventional swimming pools generally have a large number of outlets and inlets, from where water is withdrawn and returned to the pool respectively, in order to achieve proper mixing of the water volume and to actually move all that water volume contained in the pool through the filters, and to avoid potential "dead zones" that may occur within the swimming pool volume.

"Dead zones" are zones within swimming pools where the volume of water is relatively stagnant and has no significant movement or mixing, and therefore it is unlikely to be withdrawn from the pool and sent to the filtration system. Such dead zones can then start to accumulate particles, contaminants and/or sediments, or may be prone to biological proliferation, which can cause serious sanitary risks to bathers in contact with such zones.

In larger water features, the use of conventional swimming pool technology is very difficult to apply, but even more importantly the use of conventional swimming pool filtration technology is extremely challenging, as such large water features would require a very large number of outlets and inlets evenly distributed throughout the complete pool water body to achieve proper mixing and withdrawal rates that minimize the formation of dead zones. Further, in order to be able to provide all of these outlets and inlets, a very intricate and large piping network would be required, with very long piping distances that could be subject to head loss and therefore require the use of high-glow pumps and equipment. All of this would cause extremely high construction and operation costs, which makes it unviable to provide very large water features with conventional swimming pool filtration technology.

These challenges have also caused that there are no very large water features using conventional swimming pool construction and/or operation technology around the world, and some of the largest ones that have been built have had to be shut down given the high ongoing costs and operational difficulties, such as the Ocean Dome park pool in China, which closed back in 2007.

Therefore, there is a necessity of being able to provide direct contact recreation-suitable areas within larger water features, that achieve sanitary standards for swimming and that are economically viable compared to the use of conventional swimming pool technology.

BRIEF DESCRIPTION OF THE DRAWINGS

In the drawings in which the elements are identified with the same designation numeral.

DESCRIPTION OF THE INVENTION

Figure 1:
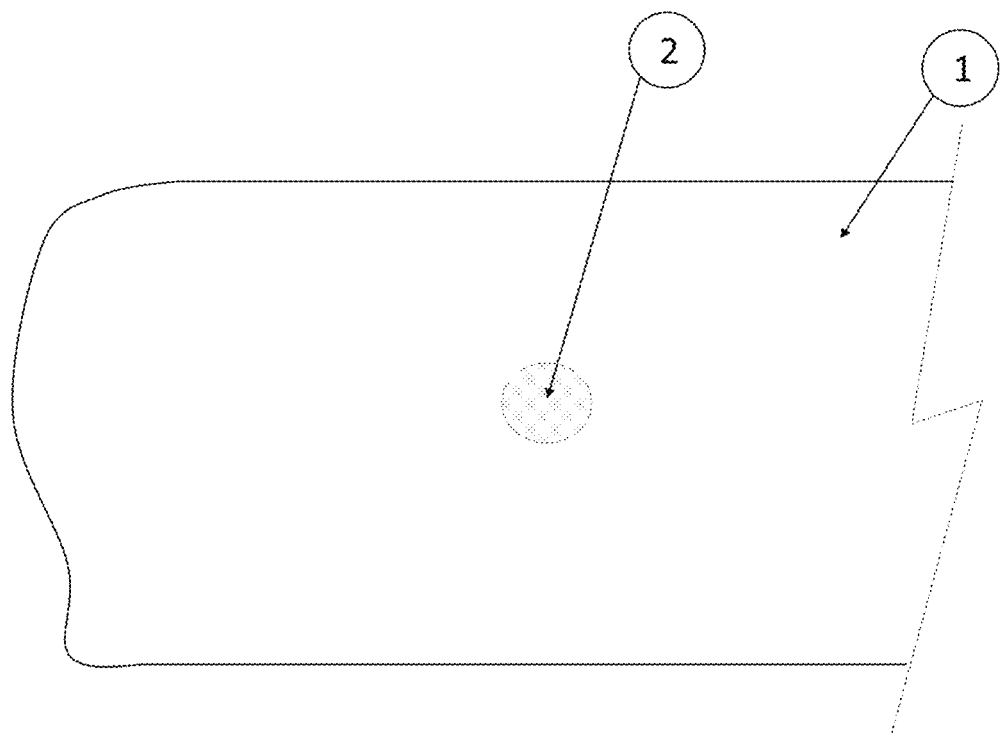
FIG. 1 shows a schematic of an embodiment of the invention, where a large water body (1) is shown, having a central circle-shaped geometric freshwater area (2).

The present invention provides for a method for creating geometric freshwater sanitary areas within large water bodies. The water bodies referenced in the present invention are man-made water bodies larger than 4,000 m² in water surface and having more than 5,000 m³ in water volume, where such water bodies include design features and operational standards suitable from a sanitary perspective to allow direct contact purposes, such as swimming and bathing, in at least some portion of the water body. Such portion of the water body is a non-physically confined portion, having a defined geometry and location. As used herein, non-physically confined portion refers to a portion of the large water body that may or may not have some visual delimitation elements such as the use of buoys or floating elements, visual markers located in the bottom and/or walls of the water feature, among other elements, however it does not comprise the use of physical barriers or walls that completely separate the volume of water of such portion from the rest of the large water body.

This innovative approach has the potential to revolutionize the recreational water feature market. It enables the design, construction, or transformation of such water features by incorporating geometric freshwater areas that meet high sanitary standards. What sets this method apart is its cost-effectiveness compared to traditional swimming pool filtration technologies. By focusing on specific areas for bathing within larger water bodies, while separately focusing on other areas for the practice of water sports, therapeutic purposes, and/or aesthetic purposes, this method significantly reduces operational costs while maintaining the required water quality, thereby offering a more efficient and economically viable solution. This advancement could lead to a paradigm shift in how recreational water features are conceptualized and operated, providing safe, sanitary swimming areas at a fraction of the usual cost.

The method of the present invention allows generating defined geometric freshwater areas, which are created within a larger surface area of a water body or water feature, through the use of a coordinated reference system (CRS) that allows mapping the defined geometric freshwater area in terms of its position; the definition of directional vectors (DVs) for the introduction of freshwater into the geometric freshwater area through inlet elements to achieve a minimum renewal rate of such geometric freshwater area; the application of a Comparative Water Renewal Index (CWRI); and the application of a Homogeneity Index (HI) based on the mixing conditions of the geometric freshwater area and its required homogenous conditions. All of these processes allow generating geometric freshwater sanitary areas that are suitable for bathing (direct contact purposes) with a building and operating cost of up to 20 times lower than for a conventional water feature that has filtration of the complete water volume of the water feature homogeneously 4 times per day (as conventional swimming pool technology).

As an example, for a 3 hectare water body (30,000 m²) with dimensions of about 100 m×300 m, swimming pool regulations (2023 Florida Building Code, Building, Eighth Edition) would require the use of at least 700 inlets, and filters that have sufficient capacity to provide a complete turnover of water in 6 hours or less to be used as part of the filtration system. Therefore, the filters would need a combined filtration capacity of 7,500 m³/h (assuming a volume of 45,000 m³ for the water body).

The present disclosure, in an innovative and new manner, allows the use of large water features (either natural or artificial) for direct contact purposes, such as swimming, in a safe and sanitary suitable manner, requiring less equipment and achieving lower costs than, for example, using conventional swimming pool filtration construction and operation technologies. This concept may cause a revolution in the recreational water feature market, by allowing to design, build, or even transform these types of water features and incorporate geometric freshwater areas that achieve sanitary-suitable water quality standards at low costs compared with conventional filtration swimming pool technologies.

In practice nowadays, only a small portion of large recreational bodies of water are designated, optimized and utilized for direct contact activities like swimming and bathing, while the most part of such water bodies is generally only used for the practice of aquatic sports. Therefore, this innovative approach ensures that while a smaller geometric freshwater area is maintained at optimal sanitary conditions for bathing, the larger water body can still be enjoyed for various recreational purposes. Thus, the invention presents a sustainable, cost-effective solution, catering to diverse recreational needs within large man-made water features while ensuring the safety and enjoyment of all users.

Definitions

As used herein, a defined geometric freshwater area is an area that is defined through a Coordinated Reference System (CRS), and that is configured to be a portion of a larger surface area of a larger water body or water feature, wherein such portion is not physically confined, as previously defined.

As used herein, a coordinated reference system (CRS) defines, with the help of coordinates based on an initial reference point (IRP), how the two-dimensional, projected defined geometric freshwater area is located within the larger water body's surface. However, it is crucial to recognize that this specification includes the utilization of alternate methodologies for such delineation. If necessary, and equivalent in effectiveness to the CRS, alternative systems or methods can be employed. For instance, zones could be delineated within an original blueprint, offering a different approach to defining these areas. This flexibility in the design and implementation process allows for the adaptation of this invention to a wide range of contexts and design preferences. By accommodating various methods for defining these zones, the invention broadens its applicability and enhances its utility in the recreational water feature market, ensuring it can meet diverse needs and requirements.

A variety of inlet elements can be used to ensure effective water circulation and quality, including skimmers, floor inlets, wall inlets, gutter systems, over-the-wall inlets, jet inlets, circular inlets, and similar nozzles.

As used herein, directional vectors (DVs) define the direction and flow of a water volume that is introduced to the geometric freshwater area. The directional vectors are defined based on the type of inlet element that is used for the introduction of such water flow, the water flow ranges allowed for such inlet element, and maximum reach conditions of such inlet element. The directional vectors that result from the inlet elements can comprise single vectors (for example, for targeted jet nozzles or similar nozzles) or multi-vectors (for example, for circular inlets or inlets with multi-directional flows).

As used herein, freshwater is water that is introduced into the geometric freshwater area, and comprises:
water with different salinities (fresh water with a salinity of less than 500 ppm, brackish water with a salinity of within 500-1,500 ppm, and salty water with a salinity of more than 1,500 ppm)
water from different sources, such as water from a well, from a natural or man-made water body, from a reservoir, from natural sources, from treated sources, and/or from filtered sources.

As used herein, direct contact recreational regulations refer to the United States Environmental Protection Agency (EPA) Direct Contact Regulations for recreational uses (2012 EPA's Criteria for Bathing (Full Body Contact) for Recreational Waters).

Embodiments

The method of the present disclosure allows generating at least one geometric freshwater area that is configured to achieve minimum water quality standards suitable for direct contact recreational purposes, such as swimming and bathing. The water body may also have other uses and purposes outside of the geometric freshwater areas, such as for the practice of water sports, therapeutic purposes, and/or aesthetic purposes. In order to apply the method of the present disclosure, the large water features comprise at least one geometric freshwater area, and the rest of the water surface and/or volume is referred to as the bulk water area (which does not comprise the geometric freshwater areas).

The method of the present application is related to the renewal of the geometric sanitary areas in order to achieve suitable water quality in such areas for direct contact recreational purposes, such as swimming. The present application does not refer to the filtration of water that is withdrawn from the geometric sanitary area, filtered and the returned to the same area, but to the renewal of water within the geometric sanitary area with freshwater that proceeds in its majority from other sources or from other location within the water body (but not the same geometric sanitary area), as it will be discussed below.

It's important to highlight that, according to the present disclosure, the freshwater is the water that is introduced to the geometric freshwater area. From a salinity standpoint, the freshwater comprises water with different salinities, and is selected from the group comprising fresh water with a salinity of less than 500 ppm, brackish water with a salinity of within 500-1,500 ppm, or salty water with a salinity of more than 1,500 ppm, as well as combinations thereof. From a source perspective, the freshwater comprises water from different sources, and can be selected from the group comprising water from a well, from a natural or man-made water body, from a reservoir, from natural sources, from treated sources, and/or from filtered sources, as well as combinations thereof.

Given that the present disclosure relates to the renewal of water and not the filtration of water, it is important to highlight that the majority of freshwater that is introduced to a geometric freshwater area must be withdrawn from another location within the large water body, or proceed from other sources, but from outside of such geometric freshwater area. When a water flow is withdrawn from a geometric freshwater area, filtered and/or treated, and then returned to the same geometric freshwater area, such recirculation is not renewal as described in the present disclosure. In a preferred embodiment of the present invention, at least 80% of the freshwater flow introduced to a geometric freshwater area proceeds from outside of such geometric freshwater area or from other sources.

In that sense the method according to the present application requires that the geometric freshwater area is defined through a coordinated reference system (CRS) that allows mapping such geometric freshwater area in terms of its position. The CRS is defined with an initial reference point (IRP), defined as (0,0) in the horizontal axis (x-axis) and vertical axis (y-axis), and from which two different sets of coordinates are defined:
Water body perimeter coordinates (3)
Geometric freshwater area coordinates (4)

Within the geometric freshwater area, a coordinated reference system (CRS) is able to map such area, an initial reference point (IRP) in such geometric freshwater area from which the coordinates defining the perimeter of the water body and the coordinates of the geometric freshwater area are established. The determination of the geometric freshwater area, the CRS, and the IRP may be carried out or decided within the design process of the large water bodies, and/or within the construction or implementation process of such large water bodies, in order to allow the method of the present invention to be performed.

This mapping is important to solve the technical problem, as is not a mere identification of locations, but instead crates a whole coordinated reference system which allows to define precise inlet elements positions and directional vectors (DVs) as explained further below.

The geometric freshwater area can be determined through plans, schematics, empirical methods, previously known or defined areas, defined by investigation, defined by reasoning, and/or defined by calculations, and combinations thereof.

Figure 2:
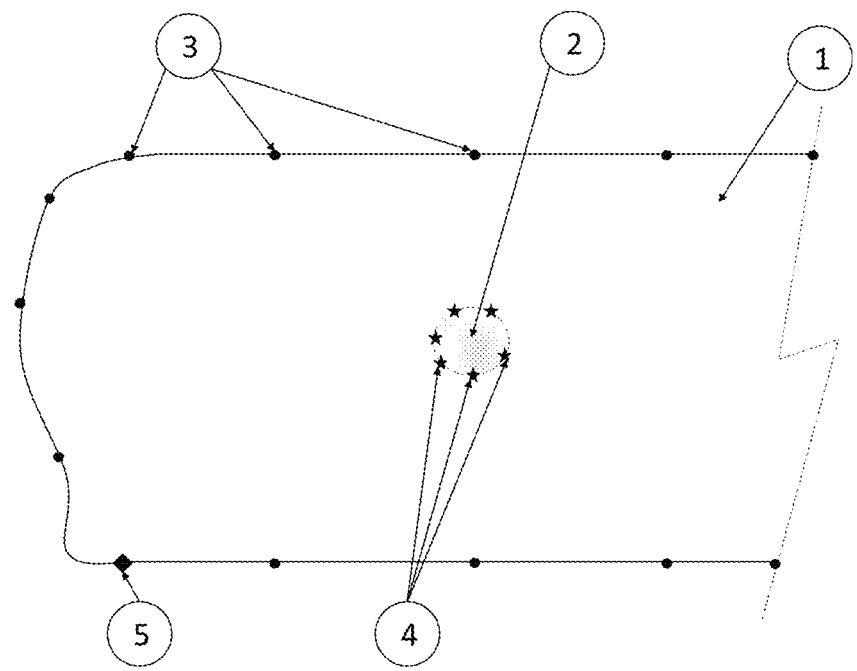
FIG. 2 shows a schematic of an embodiment of the invention, where a large water body (1) is shown, having a central circle-shaped geometric freshwater area (2), and where reference points (3) have been added in the perimeter of the large water body (1), shown as small dots. Additionally, geometric area reference points (4) have been added, shown as small stars in the Figure. An initial reference point (IRP) (5) is also shown.
Figure 3:
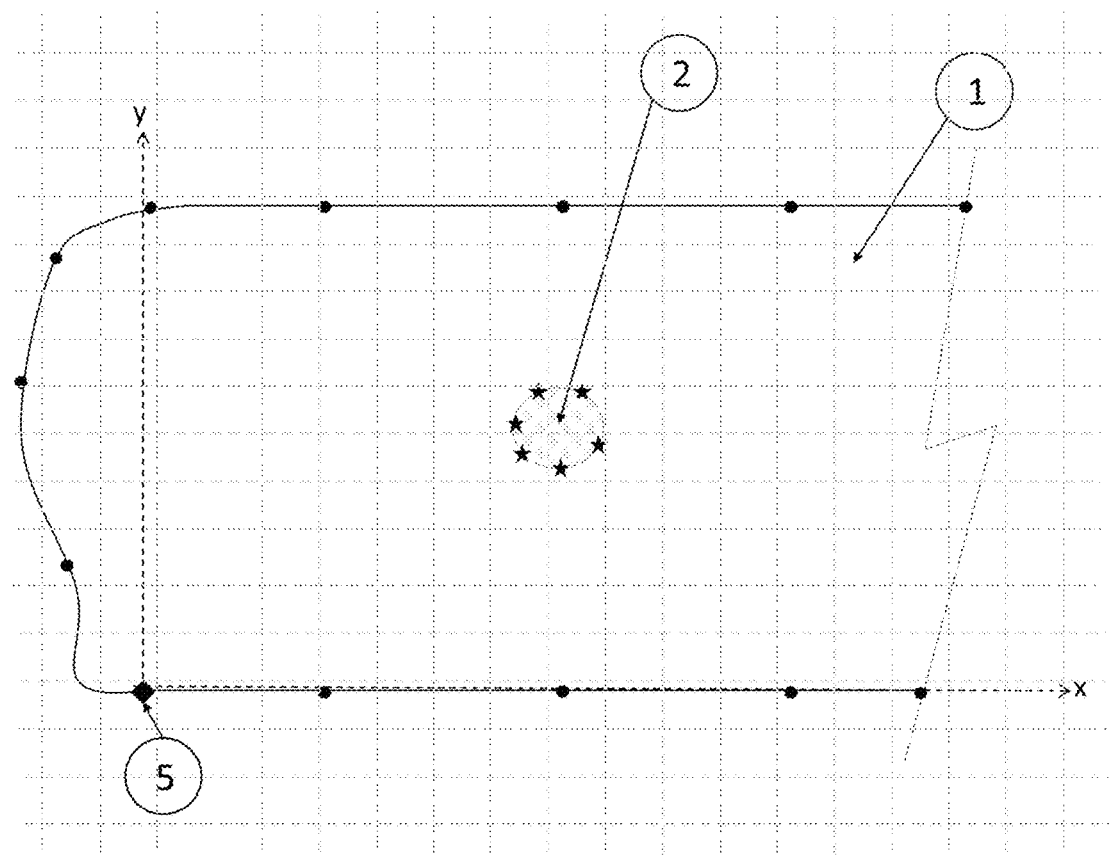
FIG. 3 shows a schematic of an embodiment of the invention, where a large water body is shown, having a central circle-shaped geometric freshwater area, and showing a referential imaginary grid with the x-axis and the y-axis starting at the IRP (5).

As an example, see FIG. 2 where the water body perimeter coordinates are shown as small dots, and where the geometric freshwater area coordinates are shown as small stars. Such coordinates are defined in terms of its horizontal and vertical distance from an initial reference point, shown as a diamond with reference numeral (5) in the same Figure. Therefore, each reference point for the water body and the geometric freshwater area will be based on the location of the initial reference point (IRP), as seen from a top view of the surface of the water body and by drawing an imaginary reference guide to determine the locations of each reference point, as seen in FIG. 3. The CRS and/or the IRP may also be defined and/or determined through other methods, such as visual inspection, physical layout of the reference system, through the use of physical elements placed throughout the water feature, empirical methods, among others.

After the initial reference point is defined, as well as the water body perimeter coordinates and the geometric freshwater area coordinates, then the average depth and reference volume is calculated for the geometric freshwater area, in order to define the volume of water contained in the geometric freshwater area.

The method of the present disclosure requires that, for water bodies that have some level of filtration, it's important to define the Comparative Water Renewal Index (CWRI), which is an index that compares the water renewal rate of a geometric freshwater area divided by the water filtration rate of the main volume of the large water feature (bulk water area) that does not comprise any geometric freshwater area. For the purposes of the present application, and to clarify the difference with a traditional filtration system, the Comparative Water Renewal Index for the present application is required to be at least 2.5, which means that the renewal rate of the geometric freshwater area is required to be at least 2.5 times larger than the filtration rate of the bulk water volume. As an example, if the water body has a filtration rate of 2 times per day, then the renewal rate of the geometric freshwater area must be at least 5 times per day, namely, at least 2.5 times larger than the filtration rate of the bulk water area according to the method of the present invention.

Further, the renewal rate of the geometric freshwater area is calculated as the volume of freshwater that is introduced into the geometric freshwater area in 24 hours compared to its total volume, as seen below:

$$\text{Renewal rate } [\text{day}^{-1}] = \frac{\text{Volume of water introduced to the geometric area } [m^3 * \text{day}^{-1}]}{\text{Total volume of the geometric area } [m^3]}$$

The renewal rate is measured as the number of hours that it takes to renew the total volume of water contained in the geometric freshwater area, and it depends on the amount of freshwater that is introduced to the geometric freshwater area. The renewal rate is related to freshwater that is introduced to such geometric freshwater area, where such freshwater is required to comply with specific parameters as previously defined.

The method of the present application requires a renewal rate of the geometric freshwater area to be at least 3.5 times per 24 hours, which means that the volume of freshwater introduced into the geometric freshwater area in a day (24 hours) is at least 3.5 times the total volume of the freshwater area.

The use of any renewal rate within the defined range is a definition performed by the owner, operator, administrator, coordination means, or any person with the capacity of modifying the renewal rate of such geometric freshwater area.

Now, given the minimum renewal rate defined for the geometric freshwater area, and since the volume and shape of the geometric freshwater area has been defined, the type of inlet elements that are to be used in the system and their corresponding directional vectors (DVs) are defined.

The inlet elements can comprise different types of nozzles including skimmers, floor inlets, wall inlets, gutter systems, over-the-wall inlets, jet inlets, circular inlets, injectors, valves, pipes, and similar elements that allow introducing freshwater into the geometric freshwater area, and that may have different flow ranges and may be of different materials depending on the specific parameters of the water body and geometric freshwater area. The inlet elements have a water flow of within 0.3-36 $m^3$/h each, which is defined based on the geometric freshwater area volume and surface, regulations, and/or safety measures, among others.

The location of the inlet elements will be defined based on the directional vectors (DVs) and the configuration of the geometric freshwater area, where the inlet elements are placed using directional vectors to achieve reaching all parts of the geometric freshwater area water volume and achieve the renewal rates of the geometric freshwater area.

The directional vectors (DVs) define the direction and flow of a water volume that is introduced to the geometric freshwater area are defined based on the type of inlet element that is used for the introduction of such water flow, the water flow ranges allowed for such inlet element, and maximum reach conditions of such inlet element.

The directional vectors that result from the inlet elements can comprise single vectors (for example, for targeted jet nozzles or similar nozzles) or multi-vectors (for example, for circular inlets or inlets with multi-directional flows), and the degree of coverage will depend on the type of inlet element and its location within the freshwater area (in sloped areas, vertical areas, flat areas, or other locations). As examples, there are inlet elements with a predominantly straight angle, while there are inlet elements that can provide a water flow in a 360° angle.

The inlet elements shall be well defined in terms of their allowed flow ranges and reach capacity, in order to ensure that the final placement and configuration of the inlet elements will allow treating all of the water volume contained within the geometric area, and that it will allow achieving the minimum water quality parameters desired for such area.

The inlet elements allow introducing freshwater into the geometric freshwater area, where the freshwater is required to comply with the following water quality parameters in order to achieve a sanitary quality suitable for direct contact recreational purposes:

pH: 7.0-8.3
Fecal coliforms: Absence
Total coliforms: Less than 5 MPN/100 ml
Floating oils and greases: Less than 5 mg/L
Turbidity: Less than 5 NTU
Iron: Less than 1 ppm
Manganese: Less than 1 ppm
True color at pH 7.71 Less than 20 Pt—Co
Copper Less than 2.0 ppm
Nitrates Less than 50 ppm
Zinc Less than 3 ppm The freshwater that is introduced to a geometric freshwater area is required to comply with the above water quality parameters, as the freshwater that is introduced allows to renew the volume of water within such geometric freshwater area, and therefore such parameters are required to be controlled and have been defined to solve the technical problem.

It's important to note that the present disclosure refers to the use of water renewal to achieve sanitary water quality suitable for direct contact recreational purposes in geometric freshwater areas within larger water bodies, whereas previous disclosures discuss the use of chemicals, such as disinfectants, applied locally to some areas to raise the oxidation reduction potential, not related to the renewal of water. The present disclosure uses directional vectors, specific water quality for inlet water, renewal rates, and others to achieve its objective of allowing the use of large water bodies for direct contact purposes, such as swimming, in a safe and sanitary suitable manner, requiring less equipment and achieving lower costs than, for example, using conventional swimming pool filtration construction and operation technologies. The addition of freshwater with the inlet elements and their corresponding directional vectors must have a flow and direction so that the difference in temperature, measured in ° C., within any 50-cm depth difference is less than or equal to 30% as an average measure performed in three separate locations within the geometric freshwater area. However, this may not be required when such geometric freshwater area includes the use of partial or fully confined barriers with the intention of achieving higher temperatures in such area compared to the bulk water volume temperature.

Figure 4:
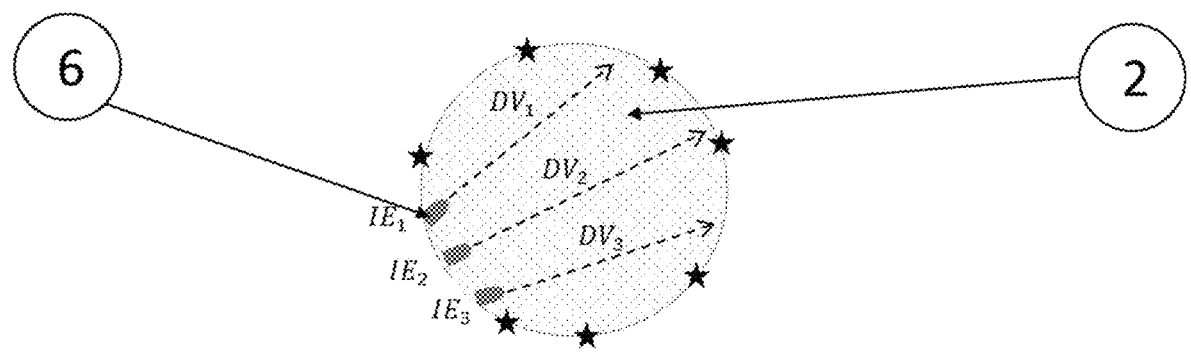
FIG. 4 shows a schematic of an embodiment of the invention according to FIG. 3, showing a close-up of a geometric freshwater area (2) shaped as a circle, and showing the location of inlet elements (6), shown as $IE_1$, $IE_2$, and $IE_3$, and their corresponding directional vectors shown as $DV_1$, $DV_2$, and $DV_3$.
Figure 5:
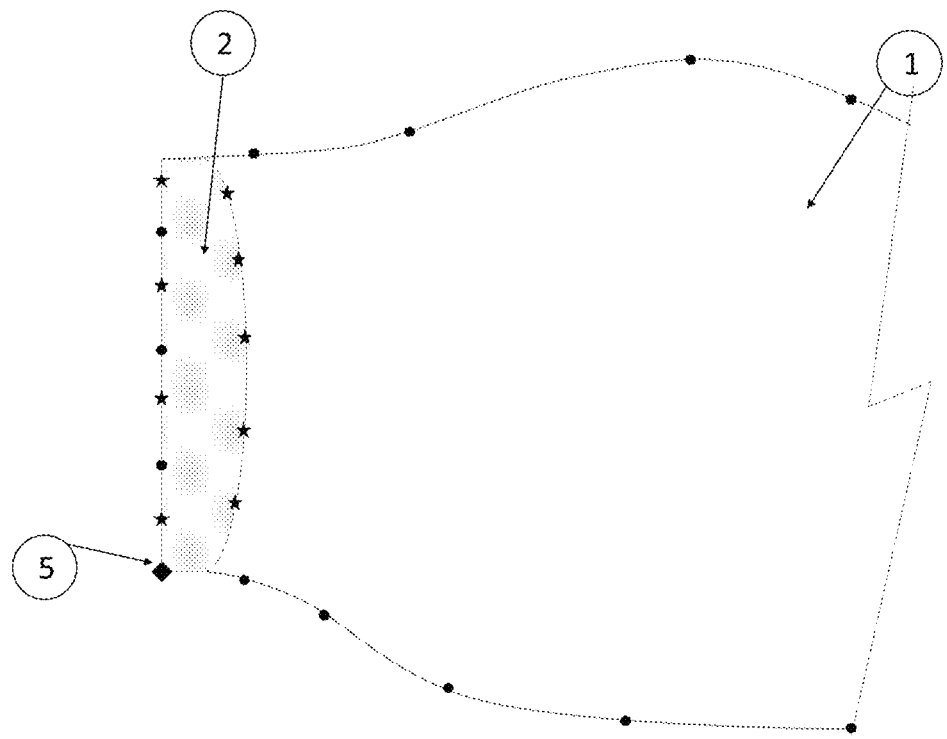
FIG. 5 shows a schematic of an embodiment of the invention, where a large water body (1) is shown, having a side semi-circle shaped geometric freshwater area (2), and where reference points (3) have been added in the perimeter of the large water body (1), shown as small dots. Additionally, geometric area reference points (4) have been added, shown as small stars in the Figure. An initial reference point (IRP) (5) is also shown.
Figure 6:
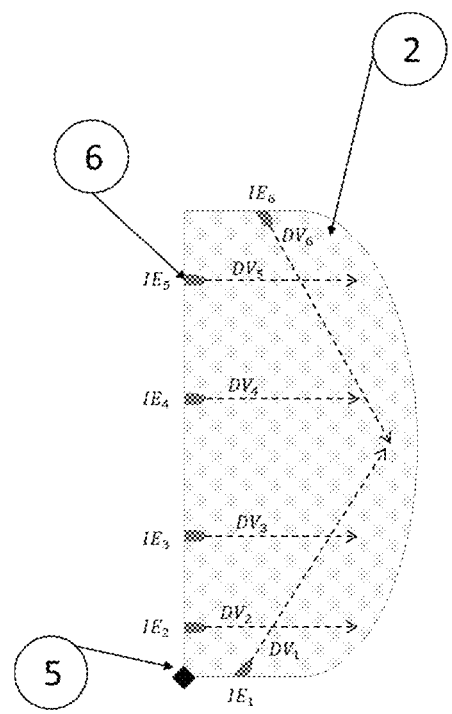
FIG. 6 shows a schematic of an embodiment of the invention according to FIG. 5, showing a close-up of a side semi-circle shaped geometric freshwater area (2), and showing the location of inlet elements (6), shown as $IE_1$, $IE_2$, $IE_3$. $IE_4$, $IE_5$, and IE6, and their corresponding directional vectors shown as $DV_1$, $DV_2$, $DV_3$, $DV_4$, $DV_5$, and $DV_6$.

For example, as seen in FIG. 4, a top view of a geometric area (2) is shown, which is located in one end of a water body (1) and that comprises six inlet elements, shown as $IE_n$, and each inlet element comprises a directional vector shown as $DV_n$, which are placed to achieve reaching all parts of the geometric area water volume where a dispersion rate is defined in order to allow a high renewal rate of the volume within the geometric area.

Once the inlet elements and their directional vectors have been defined, the method of the present application is required to comply with a Homogeneity Index related to the geometric freshwater area. As previously described, the configuration of the inlet elements and their corresponding directional vectors should be sufficient to achieve the minimum renewal rate of the geometric freshwater area, where such inlets and directional vectors are configured to achieve a Homogeneity Index as defined below.

The Homogeneity Index is related to the potential stratification or dead areas of the volume of water contained within the geometric freshwater area and its mixing conditions to show that the water inside the geometric freshwater area is new water introduced as freshwater and there is no significant permanence of water inside such area. Stratification also refers to the presence of different conditions associated with specific physicochemical parameters within the same water volume, which usually change throughout the y-axis, meaning that different values may be found at different depths. Stratification may occur with different parameters of the water, such as turbidity, salinity, temperature, among others.

In order to measure the homogeneity of a water volume, a suitable test is the use of markers or trackers that can be introduced into the geometric freshwater area and visualize/track how such markers move and eventually leave the geometric freshwater area. Types of markers and/or trackers used include the use of dyes, colorants, solutions or substances that have a residual concentration to be measured empirically, physical elements, radioactive isotopes, among others.

The Homogeneity Index is defined as follows: Homogeneity Index (HI)=1 if the difference in the tracker concentration within any 50-cm depth difference is less than or equal to 20% as an average measure performed in three separate locations within the geometric freshwater area. Otherwise, the HI is 0.

The method of the present invention requires the HI to be 1 to achieve suitable renewal of the geometric freshwater area, as well as achieving suitable direct contact recreational parameters in such area.

As used herein, the tracker concentration refers to the concentration or value of the tracker used to evaluate the homogeneity of the geometric freshwater area, which can include, for example, colorant concentration, radioactive isotope measures, visual inspection, assigning a value or category to the concentration of the tracker, among others.

According to one embodiment, the method for generating at least one geometric freshwater sanitary area within man-made large recreational water bodies, the water bodies having a surface of at least 4,000 m$^2$ and a volume of at least 5,000 m$^3$, includes determining at least one geometric freshwater area wherein a coordinated reference system (CRS) is able to map such geometric freshwater sanitary area, and determining an initial reference point (IRP) in the geometric freshwater area from which the coordinates defining the perimeter of the water body and the coordinates of the geometric freshwater area are established; determining the renewal rate of the geometric freshwater area, wherein the renewal rate of the geometric freshwater area is calculated as the volume of freshwater that is introduced into the geometric freshwater area in 24 hours compared to its total volume, and the renewal rate is at least 3.5 times per day, based on the following formula:

$$\text{Renewal Rate (Geometric freshwater area)} [\text{day}^{-1}] = \frac{\text{Volume of freshwater introduced to the geometric freshwater area} [m^3] * [\text{day}^{-1}]}{\text{Total volume of geometric freshwater area} [m^3]}$$

achieving a Comparative Water Renewal Index (CWRI) for bodies of water that include filtration, wherein the CWRI is calculated as the water renewal rate of a geometric freshwater area divided by the water filtration rate of the main volume of the bulk water area and is required to be at least 2.5, based on the following formula:

$$CWRI = \frac{\text{Renewal Rate of Geometric Freshwater Area} [\text{day}^{-1}]}{\text{Water filtration rate of bulk water area} [\text{day}^{-1}]}$$

determining the type of inlet elements used to introduce freshwater into the geometric freshwater area, and determining their Directional Vectors (DVs) according to the minimum volume of water to be introduced per unit of time to achieve the renewal rate of the geometric freshwater area and the CWRI (if applicable), wherein the inlet elements have a water flow of within 0.3 to 36 m$^3$/h each; locating the inlet elements with their corresponding directional vectors in the geometric freshwater area, wherein such inlet elements and their corresponding directional vectors are configured to achieve a Homogeneity Index (HI) of 1, wherein the HI is defined as:

Homogeneity Index (HI)=1 if the difference in the tracker concentration within any 50-cm depth difference is less than or equal to 20% as an average measure performed in three separate locations within the geometric freshwater area, wherein the tracker concentration refers to the concentration or value of the tracker used to evaluate the homogeneity of the geometric freshwater area; introducing freshwater through the inlet elements, wherein the freshwater physicochemical quality complies with the following parameters:

pH: 7.0-8.0

Fecal coliforms: Absence

Total coliforms: Less than 5 MPN/100 ml

Floating oils and greases: Less than 5 mg/L

Turbidity: Less than 5 NTU

Iron: Less than 1 ppm

Manganese: Less than 1 ppm

True color at pH 7.71 Less than 20 Pt—Co

Copper Less than 2.0 ppm

Nitrates Less than 50 ppm

Zinc Less than 3 ppm wherein the addition of freshwater through the inlet elements and their corresponding directional vectors has a flow and direction so that the difference in temperature, measured in ° C., between two points in the geometric freshwater area located at a depth difference of 50-cm, is less than or equal to 30% as an average measure of three measurements performed in three separate locations within the geometric freshwater area; and achieving a minimum water quality in the geometric area that complies with direct contact recreational regulations.

According to other embodiments, one or more of the following features may be included together with the above in combinations. First, the water body may include visual delimitation elements such as the use of buoys or floating elements, or visual markers located in the bottom and/or walls of the water feature. Second, wherein the freshwater comprises water selected from the group comprising: water from a well, water from a natural water body, water from a man-made water body, water from a reservoir, water from natural sources, water from treated sources, water from filtered sources, and combinations thereof. Third, wherein the freshwater comprises water selected from the group comprising: fresh water with a salinity of less than 500 ppm, brackish water with a salinity within 500-1,500 ppm, salty water with a salinity of more than 1,500 ppm, and combinations thereof. Fourth, wherein the freshwater that is introduced to the geometric freshwater area is withdrawn from the bulk water area. Fifth, wherein at least 80% of the freshwater that is introduced to the geometric freshwater area is withdrawn from an area outside of such freshwater area. Sixth, wherein the water body comprises other uses and purposes outside of the geometric freshwater areas including the practice of water sports, therapeutic purposes, and aesthetic purposes. Seventh, wherein the inlet elements are selected from the group comprising skimmers, floor inlets, wall inlets, gutter systems, over-the-wall inlets, jet inlets, circular inlets, injectors, valves, pipes, and elements that introduce freshwater into the geometric freshwater area. Eighth, wherein the directional vectors are selected from the group that comprise single vectors, including targeted jet nozzles, and multi-vectors, including circular inlets or inlets with multi-directional flows. Ninth, wherein the inlet elements have different flow ranges and may be of different materials depending on the specific parameters of the water body and geometric freshwater area.

Further in accordance with the previous paragraph, the following additional features and combinations may be made together, in combination, and/or together with features and combinations recited in the previous paragraph. The tenth feature includes wherein the tracker concentration comprises a colorant concentration, radioactive isotope measures, visual inspection assigning a value or category to the concentration of the tracker. Eleventh, wherein the requirement of temperature difference may not be required when such geometric freshwater area includes the use of partial or fully confined barriers with the intention of achieving higher temperatures in such area compared to the bulk water volume temperature. Twelfth, wherein the geometric freshwater area can be determined by a method selected from the group comprising determination through plans, schematics, empirical methods, previously known or defined areas, defined by investigation, defined by reasoning, and/or defined by calculations, and combinations thereof. Thirteenth, wherein determining the coordinated reference system (CRS) and/or the initial reference point (IRP) comprises utilizing methods selected from the group consisting of visual inspection, establishing a physical layout of the reference system, incorporating physical elements positioned throughout the water feature, and employing empirical methods. Fourteenth, wherein the directional vectors (DVs) of the inlet elements are adjustable, allowing for adaptability and optimization of the water flow within the geometric freshwater area. Fifteenth, wherein a dispersion rate is defined within the geometric freshwater area, thereby enabling a high renewal rate of the water volume within said geometric area. Sixteenth, wherein the homogeneity of the water volume within the geometric freshwater area can be is assessed by introducing markers or trackers to visualize or track their movement and eventual exit from the geometric freshwater area, wherein said markers or trackers are selected from the group consisting of: dyes, colorants, solutions, substances with measurable residual concentrations, physical elements, radioactive isotopes, and combinations thereof. Seventeenth, wherein the Homogeneity Index (HI) is utilized to assess potential stratification related to variations in physicochemical parameters at different depths along the y-axis within the volume of water contained in the geometric freshwater area selected from the group consisting of: turbidity, salinity, temperature and combinations thereof; or to assess the presence of dead areas.

Having described the preferred aspects and implementations of the present disclosure, modifications and equivalents of the disclosed concepts may readily occur to one skilled in the art. However, it is intended that such modifications and equivalents be included within the scope of the claims which are appended hereto.

TABLE 1

Reference Numbers from Figures

| Reference Number | Element |
| --- | --- |
| 1 | Water Body Surface Area |
| 2 | Defined Geometric Freshwater Area |
| 3 | Water Body Reference Points |
| 4 | Geometric Area Reference Points |
| 5 | Initial Reference Point |
| 6 | Inlet Elements |

What is claimed is:

1. A method for generating at least one geometric freshwater sanitary area within a man-made large recreational water body, the water body having a surface of at least 4,000 m² and a volume of at least 5,000 m³, wherein the method comprises:

determining at least one geometric freshwater sanitary area by mapping the geometric freshwater sanitary area though a coordinated reference system (CRS), wherein an initial reference point (IRP) of the geometric freshwater sanitary area is defined and from which the coordinates of the geometric freshwater sanitary area are established;

determining the renewal rate of the geometric freshwater sanitary area, wherein the renewal rate of the geometric freshwater sanitary area is determined as the volume of freshwater that is introduced into the geometric freshwater sanitary area in 24 hours compared to its total volume, and the renewal rate is at least 3.5 times per day, based on the following formula:

$$\text{Renewal Rate (Geometric freshwater area)} [\text{day}^{-1}] = \frac{\text{Volume of freshwater introduced to the geometric freshwater area } [m^3] * [\text{day}^{-1}]}{\text{Total volume of geometric freshwater area } [m^3]}$$

achieving a Comparative Water Renewal Index (CWRI) for bodies of water that include filtration, wherein the CWRI is calculated as the water renewal rate of a geometric freshwater sanitary area divided by the water filtration rate of a water area that does not include the geometric freshwater area referred to as a water area, and is required to be at least 2.5 based on the following formula:

$$CWRI = \frac{\text{Renewal Rate of Geometric Freshwater Area} [\text{day}^{-1}]}{\text{Water filtration rate of bulk water area} [\text{day}^{-1}]}$$

determining the type of inlet elements used to introduce freshwater into the geometric freshwater sanitary area and direction vectors (DVs) according to the minimum volume of water to be introduced per unit of time to achieve the renewal rate of the geometric freshwater sanitary area and the CWRI, wherein each of the inlet elements have a water flow of within 0.3 to 36 $m^3$/h;

locating the inlet elements and corresponding directional vectors in the geometric freshwater sanitary area, wherein the inlet elements and corresponding directional vectors are configured to achieve a homogeneity of less than or equal to 20%, where the homogeneity is determined by averaging the concentration difference of a tracker measured at two depths at three separate locations of the geometric freshwater sanitary area; and introducing freshwater through the inlet elements, wherein the physicochemical quality of the water within the geometric freshwater sanitary area complies with the following parameters:

pH: 7.0-8.0
Fecal coliforms: Absence
Total coliforms: Less than 5 MPN/100 ml
Floating oils and greases: Less than 5 mg/L
Turbidity: Less than 5 NTU
Iron: Less than 1 ppm
Manganese: Less than 1 ppm
True color at pH 7.71 Less than 20 Pt—Co
Copper Less than 2.0 ppm
Nitrates Less than 50 ppm
Zinc Less than 3 ppm wherein the addition of freshwater through the inlet elements and corresponding directional vectors establishes a flow and direction so that the calculated percentage difference in temperature is less than or equal to 30%, wherein the percentage difference is calculated by taking pairs of measurements at three separate locations of the geometric sanitary area, where at each of the three separate locations the pair of measurements includes a first temperature measurement and a second temperature measurement taken at a depth difference of 50 cm from the first temperature measurement, and where the percent difference between each pair of the first and the second measurements are calculated and the average percent difference is calculated for the three separate locations; and achieving a minimum water quality in the geometric freshwater sanitary area that complies with direct contact recreational regulations.

2. The method of claim 1, further including visual delimitation elements for the geometric freshwater sanitary area selected from the group including buoys or floating elements, or visual markers located at a boundary of the coordinated reference system.

3. The method of claim 1, wherein the freshwater comprises water selected from the group comprising: water from a well, water from a natural water body, water from a man-made water body, water from a reservoir, water from natural sources, water from treated sources, water from filtered sources, and combinations thereof.

4. The method of claim 1, wherein the freshwater comprises water selected from the group comprising: fresh water with a salinity of less than 500 ppm, brackish water with a salinity within 500-1,500 ppm, salty water with a salinity of more than 1,500 ppm, and combinations thereof.

5. The method of claim 1, wherein the freshwater that is introduced to the geometric freshwater sanitary area is withdrawn from the bulk water area.

6. The method of claim 1, wherein at least 80% of the freshwater that is introduced to the geometric freshwater sanitary area is withdrawn from an area outside of such freshwater area.

7. The method of claim 1, wherein the inlet elements are selected from the group comprising skimmers, floor inlets, wall inlets, gutter systems, over-the-wall inlets, jet inlets, circular inlets, injectors, valves, pipes, and elements that introduce freshwater into the geometric freshwater sanitary area.

8. The method of claim 1, wherein the directional vectors (DVs) are selected from the group that comprise single vectors, including targeted jet nozzles, and multi-vectors, including circular inlets or inlets with multi-directional flows.

9. The method of claim 1, wherein the inlet elements have different flow ranges and are constructed of different materials depending on the specific parameters of the water body and geometric freshwater sanitary area.

10. The method of claim 1, wherein the tracker concentration comprises a colorant concentration, radioactive isotope measures, visual inspection assigning a value or category to the concentration of the tracker.

11. The method of claim 1, wherein the geometric freshwater sanitary area can be determined by a method selected from the group comprising determination through plans, schematics, empirical methods, previously known or defined areas, defined by investigation, defined by reasoning, and/or defined by calculations, and combinations thereof.

12. The method of claim 1, wherein review of the coordinated reference system (CRS) and/or the initial reference point (IRP) comprises utilizing methods selected from the group comprising visual inspection, establishing a physical layout of the reference system, and incorporating physical elements positioned throughout the geometric freshwater sanitary area.

13. The method of claim 1, wherein the directional vectors (DVs) of the inlet elements are adjustable, allowing for adaptability and optimization of the water flow within the geometric freshwater sanitary area.

14. The method of claim 1, wherein a dispersion rate is defined within the geometric freshwater sanitary area, thereby enabling a high renewal rate of the water volume within said geometric area.

15. The method of claim 1, wherein the homogeneity of the water volume within the geometric freshwater sanitary area is assessed by introducing markers or trackers to visualize or track their movement and eventual exit from the geometric freshwater sanitary area, wherein the markers or trackers are selected from the group consisting of: dyes, colorants, solutions, substances with measurable residual concentrations, physical elements, radioactive isotopes, and combinations thereof.

16. The method of claim 1, wherein the Homogeneity Index (HI) is utilized to assess potential stratification related to variations in physicochemical parameters at different depths along the y-axis within the volume of water contained in the geometric freshwater sanitary area selected from the group consisting of: turbidity, salinity, temperature and combinations thereof; or to assess the presence of dead areas.

* * * * *